United States Patent
Kwok et al.

(10) Patent No.: US 6,691,708 B2
(45) Date of Patent: *Feb. 17, 2004

(54) FOREHEAD SUPPORT FOR FACIAL MASK

(75) Inventors: Philip Rodney Kwok, Chatswood (AU); William Edwin John Grant, Lanesborough, MA (US); Robert Stephen Matchett, Mosman (AU)

(73) Assignee: Resmed Limited, North Ryde (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/230,169

(22) Filed: Aug. 29, 2002

(65) Prior Publication Data

US 2003/0005935 A1 Jan. 9, 2003

Related U.S. Application Data

(62) Division of application No. 09/608,440, filed on Jun. 30, 2000, now Pat. No. 6,463,931, which is a continuation of application No. 09/008,708, filed on Jan. 16, 1998, now Pat. No. 6,119,693.

(51) Int. Cl.[7] ............................................. A62B 18/08
(52) U.S. Cl. .............................. 128/207.11; 128/201.24; 128/206.24; 128/207.17; 128/207.18
(58) Field of Search ....................... 128/207.11, 207.15, 128/207.18, 207.17, 206.24, 201.24

(56) References Cited

U.S. PATENT DOCUMENTS

| 781,516 A | 1/1905 | Guthrie |
|---|---|---|
| 812,706 A | 2/1906 | Warbasse |
| 1,081,745 A | 12/1913 | Johnston et al. |
| 1,192,186 A | 7/1916 | Greene |
| 1,653,572 A | 12/1927 | Jackson |
| 1,926,027 A | 9/1933 | Biggs |
| 2,123,353 A | 7/1938 | Catt |
| 2,245,969 A | 6/1941 | Francisco et al. |
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,376,671 A | 5/1945 | Fink |
| 2,415,846 A | 2/1947 | Randall |

(List continued on next page.)

FOREIGN PATENT DOCUMENTS

| AU | 91/77110 B | 11/1991 |
|---|---|---|
| AU | 94/64816 B | 12/1994 |
| AU | 95/16178 B | 7/1995 |

(List continued on next page.)

OTHER PUBLICATIONS

Mask 1 Photographs, Respironics Inc., Reusable Full Mask (small) Part #452033 Lot #951108.
Mask 2 Photographs, Puritan—Bennett, Adam Curcuit, Shell Part #231700, Swivel Part #616329–00, Pillows (medium) Part #616324.

(List continued on next page.)

*Primary Examiner*—Weilun Lo
*Assistant Examiner*—Darwin P. Erezo
(74) *Attorney, Agent, or Firm*—Nixon & Vanderhye P.C.

(57) ABSTRACT

An adjustable forehead support for a nasal mask. The present invention discloses an adjustable forehead support for a nasal or full-face mask wherein the forehead support may be adjusted for the different shapes and sizes of a facial profile. The forehead support utilizes a dual-arm system which adjusts the position of the forehead support vis-à-vis the mask and/or air flow tube. The angle of the mask to the face may be adjusted with the present invention.

39 Claims, 5 Drawing Sheets

U.S. PATENT DOCUMENTS

| | | |
|---|---|---|
| 2,438,058 A | 3/1948 | Kincheloe |
| 2,578,621 A | 12/1951 | Yant |
| 2,590,006 A | 3/1952 | Gordon |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher |
| 3,182,659 A | 5/1965 | Blount et al. |
| 3,189,027 A | 6/1965 | Bartlett |
| 3,193,624 A | 7/1965 | Webb et al. |
| 3,238,943 A | 3/1966 | Holley |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,700,000 A | 10/1972 | Hesse, Deceased et al. |
| 3,720,235 A | 3/1973 | Schrock |
| 3,750,333 A | 8/1973 | Vance |
| 3,752,157 A | 8/1973 | Malmin |
| 3,779,164 A | 12/1973 | Rollins |
| 3,796,216 A | 3/1974 | Schwarz |
| D231,803 S | 6/1974 | Huddy |
| 3,830,230 A | 8/1974 | Chester |
| 4,077,404 A | 3/1978 | Elam |
| D250,131 S | 10/1978 | Lewis et al. |
| 4,167,185 A | 9/1979 | Lewis |
| 4,226,234 A | 10/1980 | Gunderson |
| 4,245,632 A | 1/1981 | Houston |
| D262,322 S | 12/1981 | Mizerak |
| 4,304,229 A | 12/1981 | Curtin |
| 4,328,797 A | 5/1982 | Rollins et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,467,799 A | 8/1984 | Steinberg |
| 4,522,639 A | 6/1985 | Ansite et al. |
| 4,558,710 A | 12/1985 | Eichler |
| 4,616,647 A | 10/1986 | McCreadie |
| 4,622,964 A | 11/1986 | Flynn |
| 4,655,213 A | 4/1987 | Rapoport et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,799,477 A | 1/1989 | Lewis |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,907,584 A | 3/1990 | McGinnis |
| 4,910,806 A | 3/1990 | Baker et al. |
| 4,919,128 A | 4/1990 | Kopala et al. |
| 4,938,210 A | 7/1990 | Shene |
| 4,938,212 A | 7/1990 | Snook et al. |
| 4,944,310 A | 7/1990 | Sullivan |
| D310,431 S | 9/1990 | Bellm |
| 4,971,051 A | 11/1990 | Toffolon |
| 4,986,269 A | 1/1991 | Hakkinen |
| 4,989,596 A | 2/1991 | Macris et al. |
| 4,989,599 A | 2/1991 | Carter |
| 5,005,568 A | 4/1991 | Loescher et al. |
| 5,005,571 A | 4/1991 | Dietz |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,063,922 A | 11/1991 | Hakkinen |
| 5,069,205 A | 12/1991 | Urso |
| D323,908 S | 2/1992 | Hollister et al. |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,140,980 A | 8/1992 | Haughey et al. |
| 5,140,982 A | 8/1992 | Bauman |
| 5,159,938 A | 11/1992 | Laughlin |
| 5,178,138 A | 1/1993 | Walstrom et al. |
| D334,633 S | 4/1993 | Rudolph |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,265,595 A | 11/1993 | Rudolph |
| 5,279,289 A | 1/1994 | Kirk |
| 5,280,784 A | 1/1994 | Kohler |
| 5,311,862 A | 5/1994 | Blasdell et al. |
| 5,322,057 A | 6/1994 | Raabe et al. |
| 5,343,878 A | 9/1994 | Scarberry et al. |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |
| 5,538,000 A | 7/1996 | Rudolph |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,642,730 A | 7/1997 | Baran |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,662,101 A | 9/1997 | Ogden et al. |
| 5,666,946 A | 9/1997 | Langenback |
| 5,685,296 A | 11/1997 | Zdrojkowski et al. |

| | | | |
|---|---|---|---|
| 5,687,715 A | 11/1997 | Landis et al. | |
| 5,715,814 A | 2/1998 | Ebers | |
| 5,746,201 A | 5/1998 | Kidd | |
| 5,813,423 A | 9/1998 | Kirchgeorg | |
| 5,832,918 A | 11/1998 | Pantino | |
| 6,044,844 A | 4/2000 | Kwok et al. | |
| 6,119,693 A | 9/2000 | Kwok et al. | |
| 6,463,931 B1 * | 10/2002 | Kwok et al. | 128/207.11 |
| 6,520,182 B1 * | 2/2003 | Gunaratnam | 128/206.27 |

FOREIGN PATENT DOCUMENTS

| | | |
|---|---|---|
| AU | A 32914/95 | 2/1996 |
| AU | 9459430 | 2/1996 |
| AU | A 41018/97 | 4/1998 |
| AU | A 89312/98 | 1/1999 |
| CA | 1039144 | 9/1928 |
| DE | 459104 | 4/1928 |
| DE | 701 690 | 1/1941 |
| DE | DD 159396 | 6/1981 |
| DE | 3015279 A1 | 10/1981 |
| DE | 3345067 A1 | 6/1984 |
| DE | 3537507 | 4/1987 |
| DE | 3539073 A1 | 5/1987 |
| DE | 4004157 C1 | 4/1991 |
| DE | 4343205 A1 | 6/1995 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 A1 | 1/1988 |
| EP | 0 264 772 A1 | 4/1988 |
| EP | 0 386 605 A1 | 2/1990 |
| EP | 0427474 A2 | 5/1991 |
| EP | 0 462 701 A1 | 12/1991 |
| EP | 0 602 424 | 11/1993 |
| EP | 0 608 684 A1 | 8/1994 |
| EP | 0 0697 225 | 7/1995 |
| EP | 178 925 A2 | 4/1996 |
| EP | 0 747 078 A2 | 12/1996 |
| EP | 0 821 978 | 2/1998 |
| FR | 2 574 657 A1 | 6/1986 |
| FR | 2 658 725 A1 | 8/1991 |
| FR | 2 749 176 | 12/1997 |
| GB | 1395391 | 5/1975 |
| GB | 1 467 828 | 3/1977 |
| GB | 2145335 A | 3/1985 |
| GB | 2147506 A | 5/1985 |
| GB | 2 164 569 A | 3/1986 |
| GB | 2 267 648 A | 12/1993 |
| JP | 09/216240 A | 8/1997 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/48878 | 11/1998 |
| WO | WO 00/57942 | 10/2000 |

OTHER PUBLICATIONS

Mask 3 Photographs, DeVilbiss Healthcare Inc., Devilbiss Seal–Ring and CPAP Mask Kit (medium), Part #73510–669.

Mask 4 Photographs, Respironics Inc., Monarch Mini Mask with Pressure Port. Part #572004, Monarch Headgear, Part #572011.

Mask 5 Photographs, Healthdyne Technologies, Nasal CPAP Mask (medium narrow), Part #702510.

Mask 6 Photographs, Healthdyne Technologies, Soft Series Nasal CPAP Mask, Part #702020.

Mask 7 Photographs, DeVilbiss Healthcare Inc., Small Mask and Seal Rings, Part #73510–668.

Mask 8 Photographs, Respironics Inc., Reusable Contour Mask (medium), Part #302180.

Mask 9 Photographs, Healthdyne Technologies, Healthdyne Large Headgear.

Mask 10 Photographs, Respironics Inc., Soft Cap (medium), Part #302142.

Mask 11 Photographs, Weinmann: Hamburg, Nasalmaskensystem mit Schalldämpfer (medium), Part #WN 23105.

Mask 12 Photographs, Life Care.

Mask 13 Photographs, Healthdyne Technologies.

Mask 14 Photographs, King System.

Mask 15 Photographs, Respironics Inc., Pediatric Mask.

Mask 16 Photographs, Hans Rudolph Inc., Hans Rudolph Silicone Rubber Face Mask/8900.

Photograph of Weinmann Mask, acquired prior to 1998.

Sullivan Mirage brochure, ©1997, ResMed Limited.

Sullivan Mirage brochure, ©1998, ResMed Limited.

Somotron CPAP–Gerat WM 2300 Instruction Manual, Weinmann Hamburg, 11 pages, 1991.

9 photographs of Weinmann mask, WM 23122, 1991.

The ResMed Range of Mask Systems, product brochure, Nov. 1995, 4 pages.

* cited by examiner

FOREHEAD SUPPORT FOR FACIAL MASK

CROSS REFERENCE TO RELATED APPLICATIONS

This application is a divisional of U.S. application Ser. No. 09/608,440, filed Jun. 30, 2000, U.S. Pat. No. 6,463,931, which is a continuation of U.S. application Ser. No. 09/008,708, filed Jan. 16, 1998, now U.S. Pat. No. 6,119,693, the specifications and drawings of which are incorporated herein by reference.

FIELD OF THE INVENTION

The present invention generally relates to an improved comfort device to be used with a nasal mask. In particular, the device is useful in combination with masks which are used for the treatment of respiratory conditions and assisted respiration. The invention assists in fitting the mask to the face as well.

BACKGROUND OF THE INVENTION

Nasal masks are commonly used in the treatment of respiratory conditions and sleep disorders by delivering a flow of breathable gas to a patient to either assist the patient in respiration or to provide a therapeutic form of gas to the patient to prevent sleep disorders such as obstructive sleep apnea. These nasal masks typically receive a gas through a supply line which delivers gas into a chamber formed by walls of the mask. The mask is generally a semi-rigid mask which has a face portion which encompasses at least the wearer's nostrils Additionally, the mask may be a full face mask. The mask is normally secured to the wearer's head by straps. The straps are adjusted to pull the mask against the face with sufficient force to achieve a gas tight seal between the mask and the wearer's face. Gas is thus delivered to the mask through the aperture to the wearer's nasal passages and/or mouth.

One of the problems that arises with the use of the mask is that in order for the straps to be tight, the mask is compressed against the wearer's face and may push unduly hard on the wearer's nose. Additionally, the mask may move around vis-à-vis the wearer's face. Thus, there has been provided a forehead support, which provides a support mechanism between the mask and the forehead. This forehead support prevents both the mask from pushing too strongly against the wearer's nose and/or facial region as well as minimize movement of the mask with the addition of a contact point between the mask and the wearer's head as well as minimize uncomfortable pressure points of the mask. Additionally, the forehead support may prevent the air flow tube from contacting the wearer's forehead or face.

Prior to the present invention, the forehead supports were generally a single cushion with a single contact point which may be adjustable by rotation of a screw, with the single cushion pushing on the forehead at a single point. This is oftentimes uncomfortable for the patient, and the adjustability of the distance of the pad for different forehead protuberances oftentimes was difficult if not impossible to be performed. Additionally, a single contact point does not provide necessary lateral support to the mask. Finally, a single contact point may apply too much pressure at the single point.

Examples of prior art nasal masks are shown in U.S. Pat. Nos. 4,782,832 and 5,243,971.

There is a need for an improved forehead support for nasal and facial masks which adjusts to different angles on the face.

There is a need for a forehead support for nasal masks which may be adjusted to different forehead shapes.

There is a need for a multi-point forehead support for nasal masks.

These and other advantages will be described in more detail below.

SUMMARY OF THE INVENTION

The present invention is directed to an improved forehead support for nasal and facial masks. In particular, the present invention utilizes a dual cantilevered forehead-support which preferably utilizes dual contacts which are arranged at an obtuse angle with respect to one another and which may be easily adjusted for different forehead protuberances. Preferably, the forehead support has two arms extending from the mask or gas supply line, with the two arms engagable into a bridge system wherein the arms may be adjusted to different positions on the bridge allowing optimal positioning of the mask on the face. This achieves even pressure of the mask on the face. The mask also provides an excellent fit which limits movement of the mask during sleep. The forehead support is adjustable such that the support is closer or further away from the front plane of the facial mask. The bridge supports the pad or pads which contact the wearer's forehead. The support also may allow the mask to be secured such that more pressure is applied to one area of the mask, to seal a leak for example.

The present invention allows the mask user to adjust the angle of the mask to the face. This is possible due to the two point contact of the forehead support to the forehead working in combination with the point of contact of the mask to the face. The system thus has three points of contact, wherein the forehead pads provide two contact points and the mask to the face is a third point of contact. Adjusting the angle of the forehead pads or the distance of the legs to the forehead pads adjusts the angle of the mask vis-à-vis the face of the user. This unique system provides a mask system which can be adjusted to fit the different face angles or profiles required by users.

DETAILED DESCRIPTION OF THE PREFERRED EMBODIMENT

Figure 1:
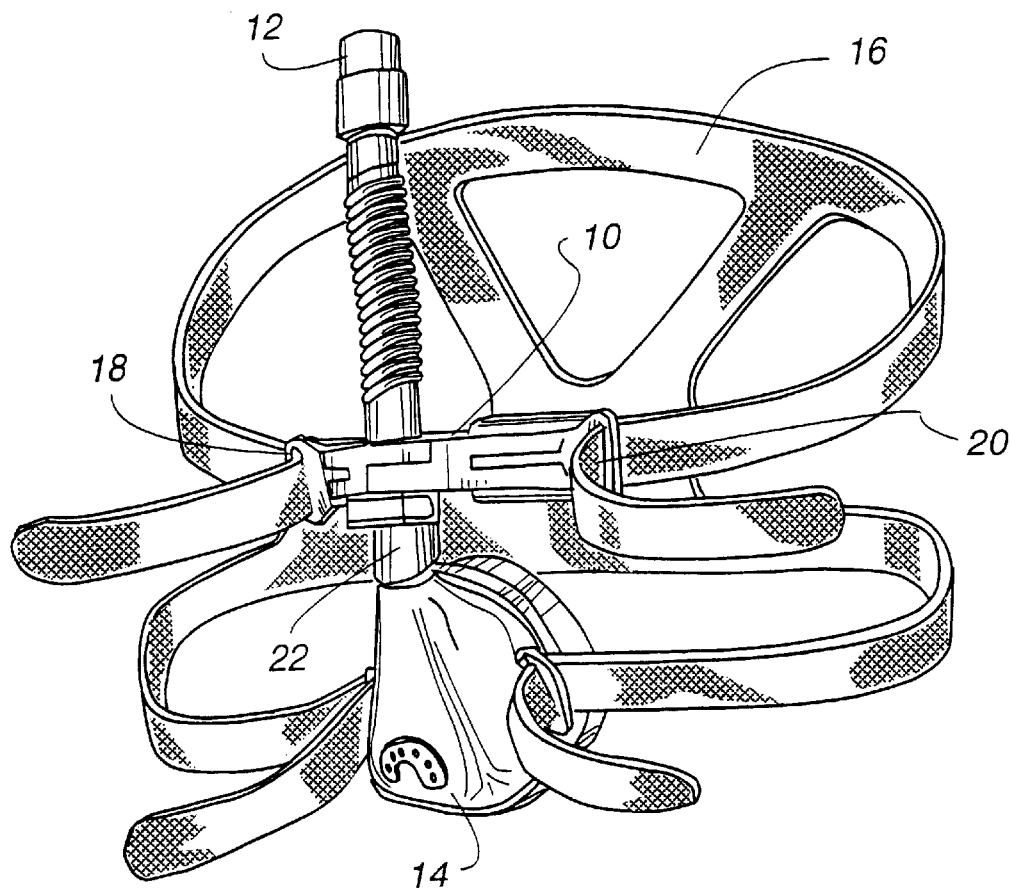
FIG. 1 is a perspective view of the forehead support of the present invention-attached to a mask, headgear and a gas supply tube.

FIG. 1 shows a general perspective view of the forehead support 10 of the present invention. The forehead rest or support 10 is attached to an extending airflow tube 12 from the mask 14. The mask 14 and forehead support 10 are shown with headgear 16 which secures the mask 14 to the head of a patient. The headgear 16 may take a variety of forms, with one example being shown as 16. As can be seen in FIG. 1, preferably the headgear 16 loops through the forehead support 10 at 18 and 20. This pulls the forehead support 10 against the forehead, thus creating a snugly fitted mask 14 and also provides a stabilizing member for the mask 14.

The mask 14, shown in FIG. 1 is merely one example of a mask which can be used with a forehead support, but any respiratory mask could be used. A full face mask which may cover the entire face or just both the nose and mouth could be used, for example. Additionally, the airflow tube 12 could be extending from the bottom of the mask 14, thus the tube 12 supporting the forehead support 10 would terminate above forehead support 10. If the airflow tube 12 extended in a downward or other direction from the mask 14, then preferably a post would extend up from the mask 14 (this post position is referenced as 22). This post 22 would terminate slightly above where forehead support 10 is shown secured to tube 12. Thus the forehead support 10 would be secured to the post in this alternative embodiment.

Figure 2:
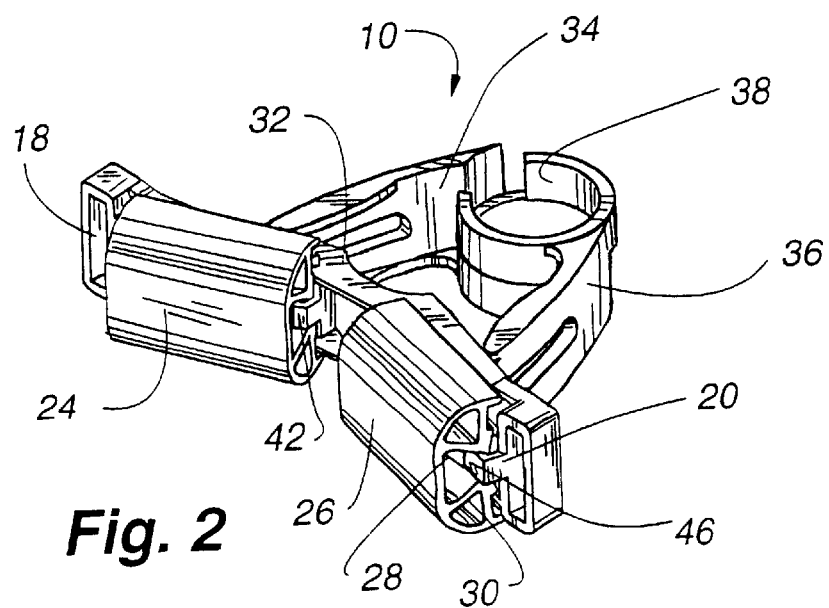
FIG. 2 is a perspective view of the forehead support of the present invention removed from the mask and gas line.

FIG. 2 discloses the preferred construction of the forehead support 10 of the present invention. The forehead support 10 has pads 24 and 26. These pads 24 and 26 are the actual contact points of the forehead support 10 to the forehead. Pads 24 and 26 are preferably made of a deformable elastomeric material which retains its original shape upon release of pressure and provides the wearer with increased comfort and stability. As can be seen in the preferred embodiment, the forehead pads 24 and 26 have an annular interior construction with two retaining walls 28 and 30. The retaining walls 28 and 30 provide structural integrity to the forehead contact support pads yet allow the pads to be deformed. The deformation preferably occurs by deflection of the pad walls. The pads also may be solid pads. The support pads 24 and 26 are mounted to the bridge 32. The bridge 32 provides basically three purposes to the forehead support 10. First off, it acts as a securing means for forehead pads or cushions 24 and 26. Second of all, it has annular spaces 18 and 20 which receive the optional headgear 16 shown in FIG. 1. Finally, it receives arms 34 and 36, which may be adjusted, as described below. The bridge 32 and arms 34 and 36 operate in a cantilever fashion and are preferably made of a polymeric material, which may be easily molded, preferably injection molded. Arms 34 and 36 are secured to bridge 32 by an adjustable locking mechanism which is better illustrated in the figures below. Additionally, arms 34 and 36 join together to create an annular space 38 which may receive airflow tube 12 which is preferably connected to a flow generator to generate breathable air or some type of therapeutic gas. Arms 34 and 36 preferably create an operational hinge. The tube 12 may be an axis of this hinge. The hinge could also be a flexible membrane and not a rotational or axial hinge. Alternatively, the tube may extend through annular space 38 and terminate as described above (in the "post" embodiment) if the air flow tube is connected to another port on the mask.

Figure 3:
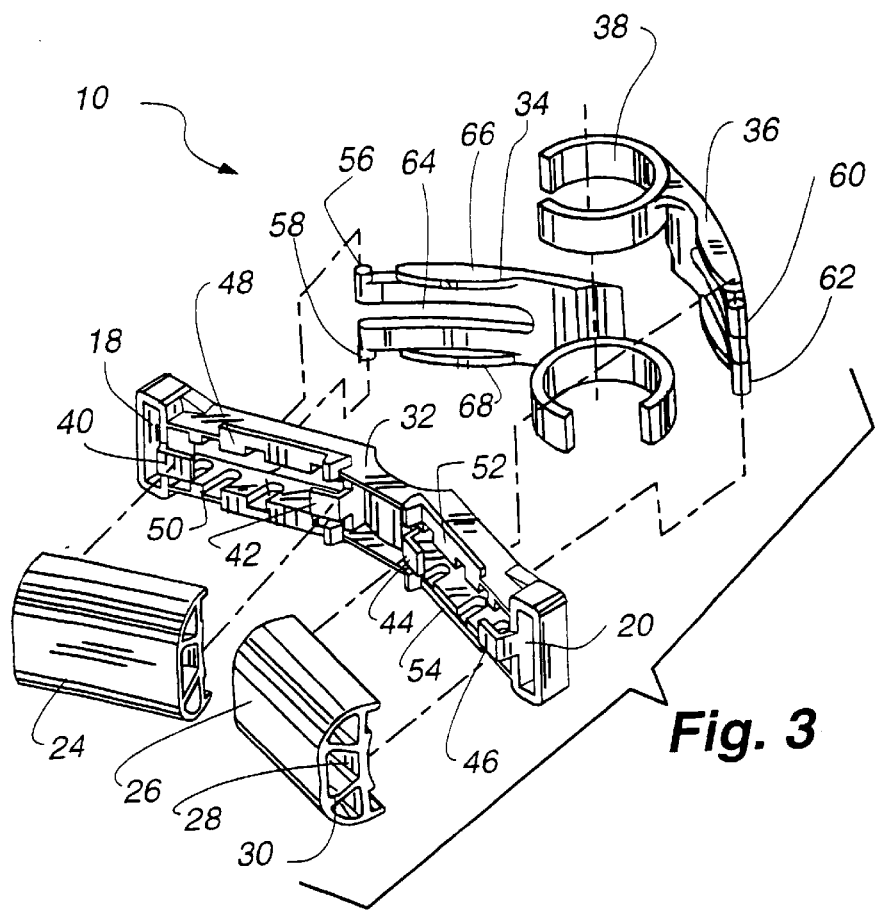
FIG. 3 is an exploded view of the forehead support of the present invention.

FIG. 3 is an exploded view of FIG. 2 and shows the forehead support 10 in greater detail. FIG. 3 discloses how bridge 32 is configured such that forehead pads 24 and 26 may be secured thereto. In particular, tongues 40, 42, 44 and 46 all engage forehead pads 24 and 26 by entering the interior space of the pads. This is shown in FIG. 2 wherein tongues 42 and 46 are shown securing pads 24 and 26 respectively by entering the annular space of the pads 24 and 26. Additionally, there may be engaging surfaces such as 48, 50, 52 and 54, as shown in FIG. 3, which engage an inner side wall of forehead pads 24 and 26. The means by which the forehead pads are secured to the bridge 32 can be done in many manners, and one skilled in the art can come up with numerous methods of achieving this securement. Two sided tape may be used, protruding pegs and apertures on the forehead pad may be used or many other methods. What is desirable is that the forehead pad(s) may be replaced after extended use or, in a clinical setting, with each new patient. The method of securement of the pad(s) to the support is not a limiting feature of the present invention.

The type of forehead pad may also vary, it may include a solid foam sponge, a stuffed pad, a dual durometer foam which may be a single pad or multiple pads attached together, or many other known pads which would impart comfort when placed directly on the forehead. Finally, a single pad which extends all the way across bridge 32 may be used or more than two pads may be used.

Bridge engaging pins 56, 58, 60 and 62 are shown in FIG. 3. As will be more apparent in the figures below, these engaging pins provide for the adjustability of the forehead support 10 of the present invention. There are pin receiving means located on the bridge 32 which receive pins 56, 58, 60 and 62. The pins 56, 58, 60 and 62 are merely one example of how the arms 34 and 36 may be secured to bridge 32. There are other designs which would work just as well as the pin designs. Such designs are known to those skilled in the art. Additionally, there is a space or recess at arms 34 and 36 shown clearly on arm 34 as 64. The purpose of this space 64 is so that the user may compress arm 34 and thus press 56 and 58 together by pressing on surfaces 66 and 68. The purpose of the compression is such that the distance between prongs 56 and 58 is decreased and thereby they may be inserted and locked into bridge 32. The structure and method of this insertion will be described in further detail below.

Figure 4:
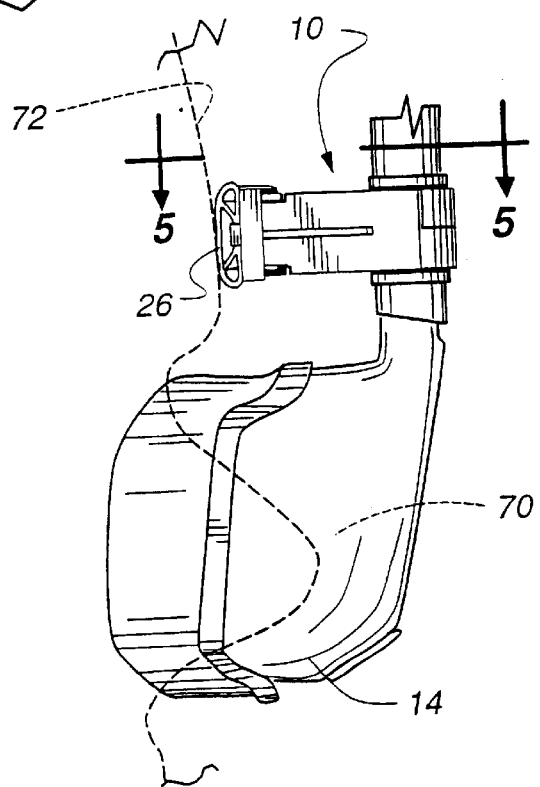
FIG. 4 is a side view of the present invention secured to a mask.

FIG. 4 is a side view of the mask 14 and forehead support 10 of the present invention. The mask is shown as 14 with a dotted line showing the nose of a wearer 70 and the dotted line showing the forehead 72 of the wearer. Pad 26 is shown compressed by the forehead of the individual wearing the mask.

Figure 5:
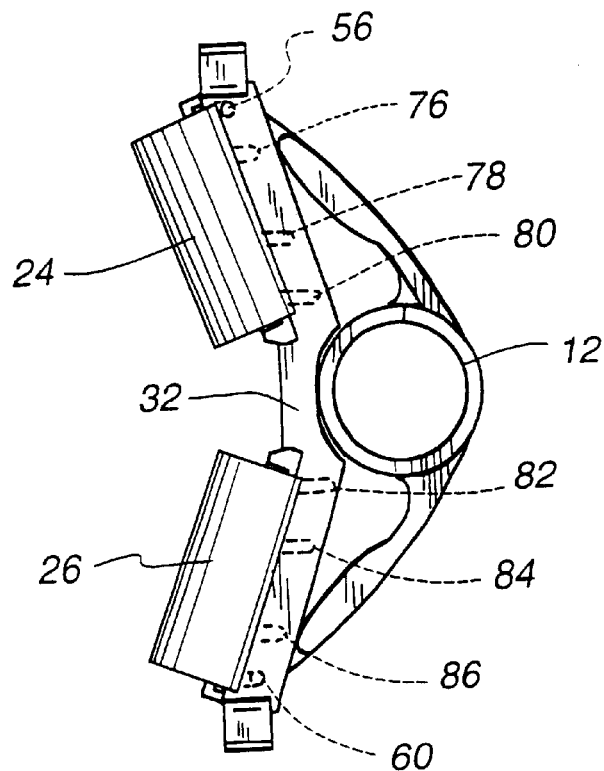
FIG. 5 is a top view of the forehead support of the present invention in a first position.

FIG. 5 is a top view of the forehead support 10 of the present invention taken along lines 5 of FIG. 4. Also, the mask 14 is not shown in FIG. 5. This figure illustrates the forehead support 10 in a position wherein the forehead support is the closest to the tube 12 (shown as merely a space in FIGS. 5–8). The bridge 32 is shown essentially in contact with tube 12. The pins 56, 58, 60 and 62 are shown in their furthest position from the center of the bridge 32. This position may be utilized by someone with a large, protruding or bulbous forehead, or a high nasal bridge, or someone who prefers the airflow tube to be snug against their forehead.

Figure 6:
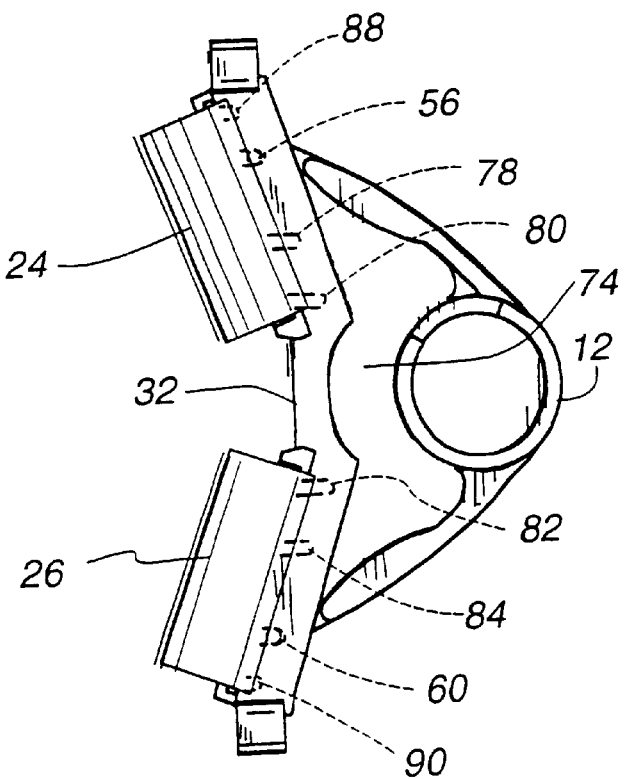
FIG. 6 is a top view of the forehead support of the present invention in a second position.

FIG. 6 shows the same forehead support in the next position, wherein the bridge 32 is moved away from tube 12 such that there is a gap 74 between bridge 32 and tube 12. As is visible from the figure, the forehead support 10 is now moved further away from tube 12, and is positioned differently than in FIG. 5. This may be configured to fit someone with a less protruding forehead, or someone who wants the flexible tube further from their head than is possible in FIG. 5.

Figure 7:
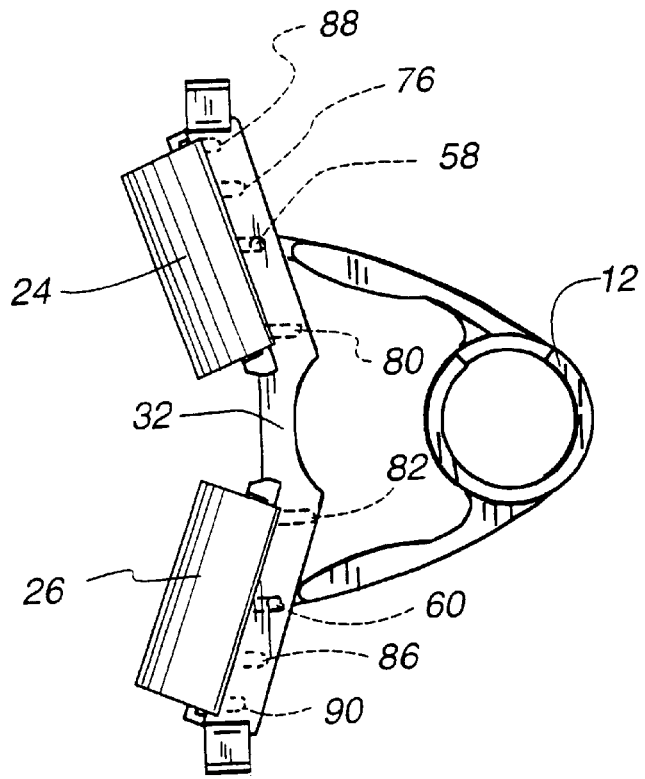
FIG. 7 is a top view of the forehead support of the present invention in a third position.
Figure 8:
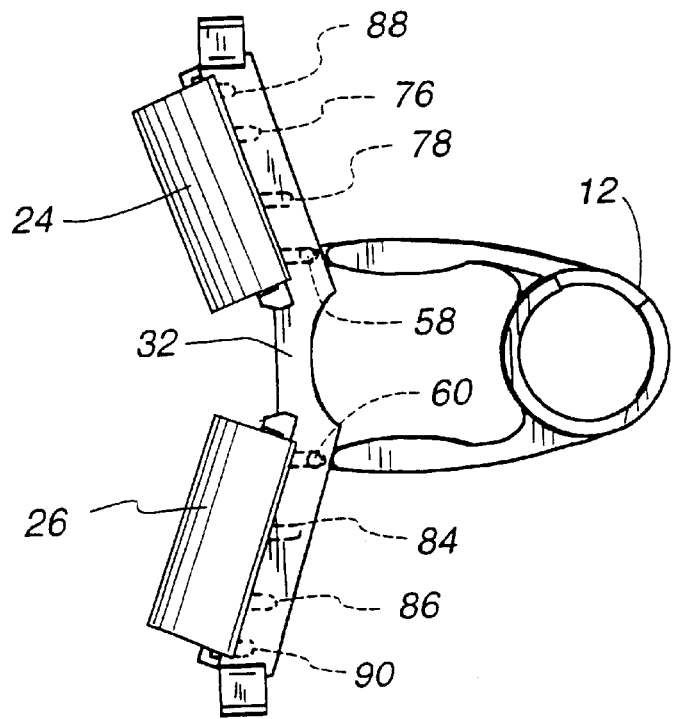
FIG. 8 is a top view of the forehead support of the present invention in a fourth position.

FIGS. 7 and 8 show the third and fourth position for the forehead support of the present invention. Although the present embodiment shows a four-positioned forehead support, the number of slots, shown as 76, 78, 80, 82, 84 86, 88 and 90 may be varied. There may be more or fewer slots, or there may just be one single slot wherein pins 56 and 58 slides transversely across bridge 32 and has locking recesses located along the slide. Additionally, the adjustments do not have to be uniform. In other words, the right side may be adjusted to slot 88 where the left side may be adjusted to slot 84 for some particular patient. There may also be more slots or adjustments on one side of the bridge as compared to the other side of the bridge. Finally, the arms may be coupled such that movement of just one arm moves the other arm in a likewise manner.

Figure 9:
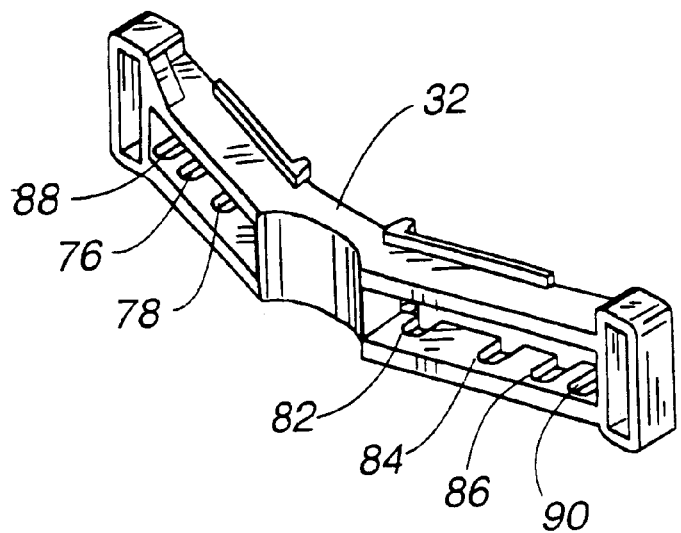
FIG. 9 is a front view of the bridge of the present invention.

FIG. 9 shows an isolated view of bridge 32. The slots 76, 78, 82, 84, 86, 88 and 90 are visible from this view. The slots are configured such that prongs 56, 58, 60 and 62 may be inserted therein. There is a mirror set of slots on the upper portion of bridge 12 which are not visible in FIG. 9. Again, there can be additional slots, fewer slots, or different methods of locking the arms 34 and 36 to various positions along the bridge 32. What is important to the present invention is that the bridge 32 with the accompanying pads 24 and 26 may be positioned to a variety of distances between the tube 12 and the pads 24 and 26. Additionally, the pad may be one continuous pad, three pads, five pads, four pads, etc. There also may a double bridge used, wherein there could be a total of two or more pads with two bridges.

Figure 10:
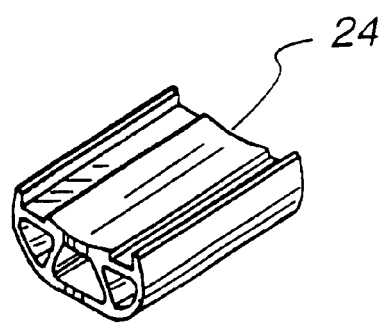
FIG. 10 is a single pad of the present invention.

FIG. 10 is a perspective view of the preferred forehead pad of the present invention. As indicated above, there could be many shapes or variations of a forehead pad and type of forehead pad or the shape of forehead pad is not limited in the present invention.

It is to be understood that while the invention has been described above in conjunction with preferred specific embodiments, the description and examples are intended to illustrate and not limit the scope of the invention, which is defined by the scope of the appended claims.

I claim:

1. A respiratory mask comprising:

a shell defining a cavity having an opening adapted to fit a respiratory opening of an individual; said shell including at least one slotted connector adapted to receive a strap to secure said mask to the individual;

a gas delivery tube connected to said shell, said gas delivery tube being adapted to supply breathable gas to said individual;

a forehead support assembly secured to an extension of said shell; said forehead support assembly including at least one pair of arms; said at least one pair of arms being configured to pivot relative to each other, and said at least one pair of arms being selectively lockable at at least two angular positions relative to each other.

2. The respiratory mask of claim 1, further comprising:

at least one forehead cushion associated with said at least one pair of arms, wherein said at least one forehead cushion comprises a surface adapted to contact a forehead of said individual.

3. The respiratory mask of claim 1, wherein said forehead support assembly comprises at least a pair of slotted connectors adapted to receive a strap to secure said respiratory mask to the individual.

4. The respiratory mask of claim 1, wherein the opening in said shell fits a nasal area of the individual.

5. The respiratory mask of claim 1, wherein the opening in said shell fits a nasal and a mouth area of the individual.

6. The respiratory mask of claim 1, wherein the opening in said shell fits a face of the individual.

7. The respiratory mask of claim 1, wherein said at least one pair of arms wrap around an extremity said gas delivery tube.

8. The respiratory mask of claim 1, wherein each of said at least one pair of arms is configured to pivot about an axis substantially parallel to an extension of said respiratory mask.

9. A forehead support assembly secured to an extension of a respiratory mask, said forehead support assembly including:

at least one pair of arms; said at least one pair of arms being configured to pivot relative to each other; and said at least one pair of arms being selectively lockable at at least two angular positions relative to each other.

10. The forehead support assembly of claim 9, further comprising:

at least one forehead cushion associated with each of said pair of arms, wherein said at least one forehead cushion comprises a surface adapted to contact a forehead of an individual.

11. The forehead support assembly of claim 9, further comprises:

at least a pair of slotted connectors adapted to receive a strap to secure said respiratory mask to an individual.

12. The respiratory mask of claim 9, wherein said at least one pair of arms wrap around an extremity of a gas delivery tube.

13. A forehead support for a respiratory mask, the forehead support comprising:

at least one pair of arms; said at least one pair of arms being configured to pivot relative to each other, said at least one pair of arms being selectively lockable at at least two angular positions relative to each other; and at least one forehead cushion associated with each of said pair of arms, wherein said at least one forehead cushion comprises a surface adapted to contact a forehead of an individual.

14. The forehead support for a respiratory mask as in claim 13, wherein said forehead support is secured to an extension of the respiratory mask.

15. The forehead support for a respiratory mask as in claim 13, further comprising:

at least a pair of slotted connectors adapted to receive a strap to secure said respiratory mask to the individual.

16. A respiratory mask comprising:

a shell defining a cavity having an opening adapted to fit a respiratory opening of an individual; said shell including at least one slotted connector adapted to receive a strap to secure said mask to the individual;

a gas delivery tube connected to said shell, said gas delivery tube being adapted to supply breathable gas to said individual;

a forehead support comprising:

at least one pair of arms; said at least one pair of arms being configured to pivot relative to each other, said at least one pair of arms being selectively lockable at at least two angular positions relative to each other; and at least one forehead cushion associated with said pair of arms,
wherein said at least one forehead cushion comprises a surface adapted to contact a forehead of an individual.

17. The forehead support for a respiratory mask as in claim 16,
wherein said forehead support is secured to an extension of the respiratory mask.

18. The forehead support for a respiratory mask as in claim 16, further comprising:
at least a pair of slotted connectors adapted to receive a strap to secure said respiratory mask to the individual.

19. An adjustable forehead support for a respiratory mask comprising:
at least one pair of arms; and
a forehead cushion associated with each of said pair of arms,
wherein each said forehead cushion comprises a surface adapted to contact a forehead of a wearer, said at least one pair of arms is configured to pivot relative to each other around a pivot axis, and said at least one pair of arms are selectively lockable at one or more angular positions relative to each other such that a distance between said pivot axis and an imaginary straight line joining each of said forehead cushions is adjusted to fit the wearer's face.

20. The adjustable forehead support for a respiratory mask of claim 19,
wherein said distance between said pivot axis and an imaginary straight line joining each of said forehead cushions increases with decreasing of an angle between said at least one pair of arms.

21. A respiratory mask comprising:
a shell defining a cavity having an opening adapted to fit a respiratory opening of an individual; said shell including at least one slotted connector adapted to receive a strap to secure said mask to the individual;
a gas delivery tube connected to said shell, said gas delivery tube being adapted to supply breathable gas to said individual;
an adjustable forehead support comprising:
at least one pair of arms; and
a forehead cushion associated with each of said pair of arms,
wherein each said forehead cushion comprises a surface adapted to contact a forehead of a wearer, said at least one pair of arms is configured to pivot relative to each other around a pivot axis, and said at least one pair of arms are selectively lockable at one or more angular positions relative to each other such that a distance between said pivot axis and an imaginary straight line joining each of said forehead cushions is adjusted to fit the wearer's face.

22. The respiratory mask of claim 21,
wherein said distance between said pivot axis and an imaginary straight line joining each of said forehead cushions increases with decreasing of an angle between said at least one pair of arms.

23. A forehead support for a respiratory mask, said forehead support including a pair of arms,
wherein each of the arms is adapted to locate a forehead cushion; the arms are adapted to pivot relative to each other; and the arms are selectively lockable at two or more angular positions relative to each other.

24. The forehead support of claim 23,
wherein the arms are also adapted to each pivot relative to the respiratory mask.

25. The forehead support of claim 23,
wherein each of the arms include a connector for a head strap.

26. A respiratory mask assembly comprising a respiratory mask and a forehead support, said forehead support including a pair of arms, wherein each of the arms is adapted to locate a forehead cushion; the arms are adapted to pivot relative to each other; and the arms are selectively lockable at two or more predetermined angular positions relative to each other.

27. The respiratory mask assembly of claim 26,
wherein the arms are also adapted to each pivot relative to the respiratory mask.

28. The respiratory mask assembly of claim 26,
wherein each of the arms includes a connector for a head strap.

29. The respiratory mask assembly of claim 26,
wherein the respiratory mask includes a connector for a head strap.

30. A respiratory mask assembly comprising:
a shell defining a cavity having an opening adapted to fit a respiratory opening of an individual, said shell including an upwardly extending support post by which, in use, breathable gas may be supplied to an interior of the shell, the shell including at least a pair of slotted connectors each adapted to receive a strap to secure said mask to the individual;
a forehead support provided to said support post, said forehead support including a bridge assembly including a plurality of first lock portions and a pair of laterally spaced forehead pads adapted to contact the individual's forehead; and
an adjustment assembly including at least one flexible portion selectively coupled to and decoupled from the bridge assembly, said adjustment assembly including a plurality of second lock portions engageable with the plurality of first lock portions of the forehead support, such that the bridge assembly is selectively lockable relative to the support post in at least four positions to provide variable transverse spacing of the bridge assembly from the individual's forehead.

31. The respiratory mask of claim 30,
wherein said bridge assembly comprises at least a pair of slotted connectors adapted to receive a strap to secure said respiratory mask to the individual.

32. The respiratory mask of claim 31,
wherein the opening in said shell fits a nasal area of the individual.

33. The respiratory mask of claim 30,
wherein the flexible portion of the adjustment assembly includes a pair of arms that are spaced apart with a gap therebetween, whereby the arms are compressible toward one another into the gap to decouple the first and second lock portions, to thereby allow adjustment of the bridge assembly.

34. A respiratory mask assembly for a patient comprising:
a mask shell coupled to a facial cushion support structure including a cheek region, a lip region and a nasal bridge region, the mask shell including a support post extending upwardly above the nasal bridge region of the facial cushion support structure; and a forehead support secured to the support post, said forehead support including an adjustment mechanism secured to the support post and a cushion frame, wherein the cushion frame is adapted to locate at least one forehead cushion and wherein the adjustment mechanism includes a flexible member that is lockable with respect to the forehead support so as to allow the cushion frame to be positioned in at least four positions relative to the support post, thereby enabling variable positioning between the patient's forehead and the forehead support.

35. The assembly as claimed in claim 34, wherein the cushion frame includes a pair of connectors each structured to releasably receive a head strap.

36. The assembly as claimed in claim 35, wherein the mask shall include a pair of connectors each structured to receive a head strap.

37. The assembly as claimed in claim 34, wherein the at least one forehead cushion spans enough of a user's forehead to promote stability.

38. The support as claimed in claim 37, wherein said at least one forehead cushion includes at least two horizontally spaced forehead cushions.

39. A respiratory mask assembly for a patient comprising:

a mask shell coupled to a facial cushion support structure including a cheek region, a lip region and a nasal bridge region, the mask shell including a support post extending upwardly above the nasal bridge region of the facial cushion support structure;

a forehead support provided to the support post, said forehead support including an adjustment mechanism secured to the support post and a cushion frame, wherein the cushion frame includes a bridge, and wherein the adjustment mechanism includes at least one portion that is movable relative to the support post such that, in use, the cushion frame is movable toward and away from the patient's forehead, and a pair of forehead cushions provided on the bridge, the forehead cushions being spaced from one another along a length of the bridge with a space being provided between a center portion of the bridge and the patient's forehead, wherein the adjustment mechanism is constructed and arranged to selectively lock the bridge relative to the mask in at least three predetermined positions, each of the forehead cushions includes an inner wall abutting a surface of the bridge and an outer wall adapted to be in contact with the patient's forehead, each of the forehead cushions is made of a deformable material that retains its shape, the bridge includes a retainer element provided on each lateral end of each of the forehead cushions, and each of the forehead cushions includes a surface engaged with a respective one of said retainers, and the bridge is substantially wider than the support post.

* * * * *